United States Patent
Mirejovsky et al.

(10) Patent No.: US 7,153,840 B2
(45) Date of Patent: Dec. 26, 2006

(54) AQUEOUS FLUDARABINE PHOSPHATE COMPOSITION

(75) Inventors: Dorla Mirejovsky, Irvine, CA (US); Peter Lindsay Macdonald, Gentilino (CH)

(73) Assignee: Sicor, Inc., Irvine, CA (US)

( * ) Notice: Subject to any disclaimer, the term of this patent is extended or adjusted under 35 U.S.C. 154(b) by 0 days.

(21) Appl. No.: 10/445,306

(22) Filed: May 23, 2003

(65) Prior Publication Data

US 2004/0006041 A1    Jan. 8, 2004

Related U.S. Application Data

(60) Provisional application No. 60/383,408, filed on May 24, 2002.

(51) Int. Cl.
*A61K 31/7076* (2006.01)

(52) U.S. Cl. .............................. 514/45; 514/46; 514/48; 514/388; 514/449; 424/457; 424/458; 424/460; 424/463; 424/469; 424/470; 536/55.3; 536/27.12; 536/26.71

(58) Field of Classification Search .................. 514/45, 514/46, 48, 388, 449; 424/457, 458, 460, 424/463, 469, 470; 536/55.3, 27.12, 26.71
See application file for complete search history.

(56) References Cited

U.S. PATENT DOCUMENTS

| | | | | |
|---|---|---|---|---|
| 4,988,722 | A | * | 1/1991 | Yuen .......................... 514/383 |
| 5,081,110 | A | * | 1/1992 | Kim et al. ..................... 514/47 |
| 6,046,322 | A | * | 4/2000 | Tilstam et al. ............. 536/55.3 |
| 6,174,873 | B1 | * | 1/2001 | Wrenn, Jr. ................... 514/45 |

OTHER PUBLICATIONS

International Search Report for related PCT International Application No. PCT/US03/16395, filed May 23, 2003 (Oct. 30, 2003).

* cited by examiner

*Primary Examiner*—Shaojia Anna Jiang
*Assistant Examiner*—Devesh Khare
(74) *Attorney, Agent, or Firm*—Kenyon & Kenyon LLP

(57) ABSTRACT

This invention is directed towards a ready-to-use aqueous composition of fludarabine phosphate. In one embodiment, the invention is directed to an aqueous fludarabine phosphate composition which comprises fludarabine phosphate, a base, and water. The concentration of fludarabine phosphate in the composition may be between about 0.5 mg/mL and about 50 mg/mL. The pH of the composition may be between about 5.5 and about 7.1.

25 Claims, No Drawings

AQUEOUS FLUDARABINE PHOSPHATE COMPOSITION

This application claims priority to U.S. Provisional Application Ser. No. 60/383,408, filed May 24, 2002, the entire disclosure of which is hereby incorporated by reference.

FIELD OF THE INVENTION

The invention relates to aqueous fludarabine phosphate compositions, and to processes for their preparation.

BACKGROUND OF THE INVENTION

Fludarabine phosphate, a synthetic purine nucleoside, is an antineoplastic agent. Fludarabine phosphate differs from the physiologic nucleosides, adenosine and deoxyadenosine, in that the sugar moiety is arabinose instead of ribose or deoxyribose, respectively, and by the addition of a fluorine atom to the purine base adenine. The drug is a purine antagonist antimetabolite. Fludarabine also is structurally related to vidarabine (9-β-D-arabinofuranosyladenine, ara-A), differing only by the presence of a fluorine atom at position 2 of the purine moiety and a phosphate group at position 5 of the arabinose moiety.

Fludarabine (2-fluoro-ara-A) is commercially available as the phosphate salt (2-fluoro-ara-AMP), the structure of which may be represented as shown below:

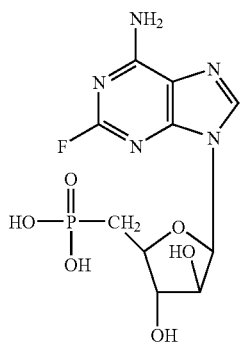

Commercially available fludarabine phosphate powder for injection is a white, lyophilized solid cake containing fludarabine (50 mg/vial) and mannitol (50 mg/vial). Following reconstitution of the drug with sterile water for injection to a concentration of 25 mg/mL, the solution has a pH of approximately 7.7. (range 7.2–8.2). After reconstitution, the product usually is combined with 100 ml or 125 ml of a pharmaceutically acceptable intravenous solution, such as aqueous 0.9% sodium chloride or 5% dextrose.

It is desirable to provide a ready-to-use stable aqueous fludarabine phosphate composition that could be administered without the need for reconstituting lyophilized fludarabine phosphate currently available. However, an impediment to the preparation of an aqueous fludarabine phosphate composition is that such compositions may not be adequately stable at ambient temperatures. Generally, ready-to-use solutions are stored and transported at refrigerated temperatures (e.g., 2° C.–8° C.) to circumvent the lower stability of ready-to-use solutions in comparison to lyophilized compositions. Still, accidental exposure of a ready-to-use compositions to elevated temperatures (i.e., temperatures at or above ambient temperature) during storage or transportation can result in unacceptable levels of degradation.

An object of the present invention is to provide a ready-to-use aqueous fludarabine phosphate composition with enhanced stability at elevated temperatures such that accidental exposure of the composition to elevated temperatures for a brief time would be less likely to result in unacceptable levels of degradation of the fludarabine phosphate.

SUMMARY OF THE INVENTION

The present inventors have found, surprisingly, that it may be possible to prepare aqueous compositions containing fludarabine phosphate having enhanced stability upon a transient exposure to elevated temperatures by controlling the pH of the fludarabine phosphate composition.

This invention is directed towards a ready-to-use injectable aqueous composition of fludarabine phosphate. In one embodiment, the invention is directed to an injectable aqueous fludarabine phosphate composition which comprises fludarabine phosphate, a base, and water, and has a pH from about 5.5 to 7.1. The concentration of fludarabine phosphate in the composition may be between 0.5 mg/mL and 50 mg/mL.

In another embodiment, the invention is directed to a method for preparing an injectable aqueous fludarabine phosphate composition according to the present invention. The method comprises combining fludarabine phosphate, water, and a base to provide a composition having between 0.5 mg/mL and 50 mg/mL fludarabine phosphate, a base, water, and a pH from about 5.5 to 7.1.

DETAILED DESCRIPTION OF THE INVENTION

The present invention is based on the discovery that an aqueous fludarabine phosphate composition having enhanced stability at elevated temperatures may be prepared by controlling the pH of the composition. The present invention is directed to an injectable aqueous fludarabine phosphate composition which comprises fludarabine phosphate, a base, and water, and has a pH from about 5.5 to 7.1.

As used herein, the term "elevated temperatures" refers to temperatures at or above ambient temperatures. The term "ambient temperature" refers to temperatures ranging from about 22° C. to about 28° C. The term "enhanced stability" refers to an aqueous fludarabine phosphate composition which, when compared to another aqueous fludarabine phosphate composition, contains at least 0.8% less of fludarabine phosphate 2-hydroxy analog and at least 1.0% less total fludarabine degradation products when both compositions are subjected to a temperature of 40° C. for a period of 1 month. For example, the term "enhanced stability" may be used to distinguish between two otherwise comparable aqueous fludarabine phosphate compositions as follows: Two aqueous fludarabine phosphate compositions, A and B, differ only in the pH of the respective compositions. Compositions A and B have pH values of 6.5 and 7.7, respectively. After storing both compositions at 40° C. for 1 month, composition A is found to contain a level of fludarabine phosphate 2-hydroxy analog that is less that the level of quantitation (i.e, less than 0.1%) and a total fludarabine phosphate impurity level of 0.2%, whereas composition B is found to contain a level of fludarabine phosphate 2-hydroxy analog of 0.8% and a total fludarabine phosphate impurity level of 1.3%. Composition A has "enhanced stability" with respect to composition B because composition B showed a level of fludarabine phosphate 2-hydroxy analog at least 0.8% greater than that of composition A and a total fludarabine phosphate impurity level at least 1.0% greater than that of composition A.

The term "comparable aqueous fludarabine phosphate composition" refers to an aqueous fludarabine phosphate composition which differs from the reference aqueous fludarabine phosphate composition only in the pH of the composition. For example, in reference to an aqueous fludarabine phosphate composition A, having a fludarabine phosphate concentration of 25 mg/ml and a pH of 6.5, aqueous fludarabine phosphate composition B, has a fludarabine phosphate concentration of 25 mg/ml and a pH of 7.7. Because composition B differs from composition A only in the pH of the composition, composition B would be a "comparable aqueous fludarabine phosphate composition" with respect to composition A. If, on the other hand, composition B had a fludarabine phosphate concentration other than 25 mg/ml (e.g., 40 mg/ml), then it would not be a "comparable aqueous fludarabine phosphate composition" with respect to composition A.

In one embodiment, the concentration of fludarabine phosphate in the composition may be between 0.5 mg/mL and 50 mg/mL. The concentration of base in the composition is that amount necessary to provide a solution having a pH within the desired range. The pH of the composition may be between about 5.5 and 7.1.

In one embodiment, the pH of the aqueous fludarabine composition is between about 6.3 and 7.1. Within this range, the pH of the aqueous fludarabine phosphate composition may be between about 6.5 and 7.1. Typically, the pH of the fludarabine phosphate composition is between about 6.7 and 6.9.

In another embodiment, the concentration of fludarabine phosphate is between 10 mg/mL and 40 mg/mL. Within this range, the concentration of fludarabine phosphate may be between 20 mg/mL and 30 mg/mL. The concentration of fludarabine phosphate may be between 24 mg/mL and 26 mg/mL. Typically, the concentration of fludarabine phosphate is about 25 mg/mL.

The compositions of this invention also may contain bulking agents, stabilizers and tonicity agents. Examples of bulking agents that may be used in the compositions of this invention include sugars, such as, for example, mannitol, lactose, sucrose, maltose and the like. These sugars may be present in an amount from about 5 mg/ml to as high as 100 mg/ml. Typically the concentration is about 25 mg/ml. As is known by those skilled in the art, some of these components also may be used as stabilizers and tonicity agents. Other tonicity agents which may be used in the compositions of this invention include sodium chloride and dextrose.

The compositions of this invention may be prepared as ready-to-use intravenous solutions. Such compositions typically include a tonicity agent in a concentration that makes the composition isotonic with a person's blood. For example, such compositions may include 0.9% NaCl or 5% dextrose.

Pharmaceutically acceptable bases that may be used in the present invention NaOH, $NH_4OH$ and KOH.

In another embodiment, the compositions of the present invention may include a buffer. The concentration of buffer may be between 5 mM and 200 mM. Within this range, the concentration of buffer may be between 5 mM and 100 mM. Typically the concentration of buffer is between 5 mM and 50 mM.

Pharmaceutically acceptable buffers which may be used in the compositions of the present invention include citrate buffers, phosphate buffers, citric acid/phosphate buffers, carbonate/carbonic acid buffers, succinate/succinic acid buffers, bis[2-hydroxyethyl]iminotris[hydroxymethyl]methane/2-bis[hydroxyethyl]amino-2-[hydroxymethyl]-1,3-propanediol) (known as "BIS-TRIS"), and (3-N-morpholino]propanesulfonic acid) (known as "MOPS"). Pharmaceutically acceptable carbonate buffers include $CaCO_3$ and $Na_2CO_3$. Pharmaceutically acceptable phosphate buffers include $Na_3PO_4$, $Na_2HPO_4$, $NaH_2PO_4$, $K_3PO_4$, $K_2HPO_4$, and $KH_2PO_4$. In one embodiment, the buffer is $Na_2HPO_4/NaH_2PO_4$. In another embodiment, the buffer is $K_2HPO_4/KH_2PO_4$.

In another embodiment, the invention is directed to a method for preparing an aqueous fludarabine phosphate composition by (a) dissolving a base in water; and (b) combining the mixture of step (a) with fludarabine phosphate. Alternatively, the invention is directed to a method for preparing an aqueous fludarabine phosphate composition by dissolving fludarabine phosphate in water and combining the aqueous fludarabine phosphate solution with a base.

The aqueous fludarabine phosphate compositions of the present invention may be useful for treating a diverse array of neoplastic diseases including chronic lymphocytic leukemia (CLL). The aqueous fludarabine phosphate compositions of the present invention also may be useful for treating acute myeloid (myelogenous, nonlymphatic) leukemia (AML, ANLL) and acute lymphocytic leukemia (ALL). These compositions also may be used to treat non-Hodgkin's lymphoma. In addition, these compositions may be used to treat prolymphocytic leukemia (PLL) and pro-lymphocytoid chronic lymphocytic leukemia (CLL-Pro).

Chemotherapeutic agents often are administered in dosages based upon the surface area of the patient. Fludarabine phosphate typically is administered as a single dose of 25 mg/m$^2$-per day for 5 consecutive days. Dosages up to 30 mg/m$^2$-per day for 5 consecutive days also may be used. As recognized by those skilled in the art, the particular quantity of pharmaceutical composition according to the present invention administered to a patient will depend upon a number of factors, including, without limitation, the biological activity desired, the condition of the patient, and tolerance for the drug. Typically, fludarabine phosphate is administered intravenously over an infusion period of about 30 minutes or by continuous IV infusion.

The present inventors have found, surprisingly, that it may be possible to prepare aqueous compositions containing fludarabine phosphate having enhanced stability upon a transient exposure to elevated temperatures by controlling the pH of the aqueous fludarabine phosphate composition. In order to prepare such compositions with enhanced stability at elevated temperatures, the pH of the aqueous fludarabine phosphate composition may be from about 5.5 to 7.1.

The effect of the pH of the aqueous fludarabine phosphate composition on the stability of the compositions at elevated temperatures is shown in the following table. The concentration of fludarabine phosphate in each of the compositions of Table 1 was 25 mg/mL.

TABLE 1

Effect of pH on Formation of Related Compounds of Fludarabine
Phosphate in Aqueous Compositions Stored at 40° C. for 1 Month

| pH of Fludarabine phosphate Composition | Concentration of FP-2HA % | Total Related Compounds* % |
|---|---|---|
| 5.5 | <LOQ | 0.1 |
| 6.5 | <LOQ | 0.2 |
| 7.7 | 0.8 | 1.3 |
| 8.1 | 1.0 | 2.2 |

FP-2HA: Fludarabine phosphate, 2-hydroxy analogue
<LOQ: Less than the level of quantitation
ND: Not detected
*excluding fludarabine The data in Table 1 demonstrate that the pH of the aqueous fludarabine phosphate compositions affects the stability of the compositions at elevated temperatures. The data in Table 1 shows an enhancement of fludarabine phosphate stability at pH levels below 7.0. For example, after 1 months at 40° C., the fludarabine phosphate composition having a pH of 5.5 contained no detectable levels of FP-2HA, which is a 2-hydroxy analogue of fludarabine phosphate. Its level of "total related compounds" was 0.1%. In contrast, after being stored for 1 months at 40° C., the fludarabine phosphate composition having a pH of 7.7 contained 0.8 of FP-2HA and 1.3% "total related compounds."

The effect of the pH of the aqueous fludarabine phosphate composition on the stability of the compositions at elevated temperatures also is shown in Tables 2 and 3. The concentration of fludarabine phosphate in each of the compositions of Tables 2 and 3 was 25 mg/mL.

TABLE 2

Effect of pH on Formation of Related Compounds of Fludarabine
Phosphate in Aqueous Composition Stored at 40° C. for 1 Month
Followed by One-Year Storage at 2–8° C.

| pH of Fludarabine Phosphate Composition | Concentration of FP-2HA, % | Single Largest Other, % | Total Related Compounds*, % |
|---|---|---|---|
| 6.0 | 0.4 | 0.09 | 0.5 |
| 7.0 | 0.32 | 0.1 | 0.34 |
| 7.6 | 0.56 | 0.2 | 1.1 |
| 8.1 | 0.93 | 0.4 | 2.0 |

FP-2HA: Fludarabine phosphate, 2-hydroxy analogue
*Excluding fludarabine

TABLE 3

Effect of pH on Formation of Related Compounds of Fludarabine
Phosphate in Aqueous Composition Stored at 27.5° C. for 7 Months

| pH of Fludarabine Phosphate Composition | Concentration of FP-2HA, % | Single Largest Other, % | Total Related Compounds*, % |
|---|---|---|---|
| 6.8 | 0.33 | 0.1 | 0.43 |
| 7.2 | 0.54 | 0.1 | 0.94 |

FP-2HA: Fludarabine phosphate, 2-hydroxy analogue
*Excluding fludarabine

The data in Tables 2 and 3 demonstrate that the pH of the aqueous fludarabine phosphate compositions affects the stability of the compositions at elevated temperatures.

The aqueous fludarabine phosphate compositions of the present invention may be stored in any suitable container that does not adversely affect the stability of the compositions. For example, suitable containers for the compositions of the present invention include glass vials and plastic vials. Suitable plastic vials include those made primarily of polypropylene, Daikyo Resin CZ (sold by Daikyo Gomu Seiko, Ltd., reported in some references as polymethylpentene) and polyethylene terephthalate.

EXAMPLE 1

A fludarabine phosphate solution (25 mg/mL) with pH of 6.8 was prepared by the following steps: Mannitol (2.5 g) was added to Water for Injection (70 mL). Solid fludarabine phosphate (2.5 g) was added with stirring to form a slurry. Aqueous sodium hydroxide (1N) was added with stirring until the pH of the solution was 6.8 and the solution was clear. Water for Injection was added to the resultant solution to bring the total volume to 100 mL.

EXAMPLE 2

A fludarabine phosphate solution (25 mg/mL) with pH of 6.5 is prepared by the following steps: About 8 mL of 1N sodium hydroxide is combined with about 70 mL Water for Injection with stirring. Fludarabine phosphate (25 mg) is added to the resultant solution with stirring. The pH of the solution is adjusted to 6.2 with 1N NaOH and Water for Injection is added to bring the total volume to 100 mL.

FORMULATION EXAMPLE 1

An aqueous solution containing an fludarabine phosphate concentration of 25 mg/mL and having the following components:

| | |
|---|---|
| Fludarabine phosphate | 25 mg/mL |
| Mannitol | 25 mg/mL |
| Sodium Hydroxide | to pH 6.8 |
| Water for Injection | q.s. to 2 mL |

FORMULATION EXAMPLE 2

An aqueous solution containing an fludarabine phosphate concentration of 25 mg/mL and having the following components:

| | |
|---|---|
| Fludarabine phosphate | 25 mg/mL |
| Mannitol | 25 mg/mL |
| Sodium Hydroxide | 3.8 mg/mL |
| 1 N Sodium Hydroxide | to pH 6.8 |
| Water for Injection | q.s. to 2 mL |

While 25 mg/mL fludarabine phosphate composition has been exemplified, solutions of different concentrations of fludarabine phosphate may be prepared according to the methods of the present invention.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following non-limiting enumerated embodiments.

What is claimed is:

1. A ready-to-use injectable aqueous pharmaceutical composition comprising:
   (a) between 0.5 mg/mL and 50 mg/mL fludarabine phosphate;
   (b) a base; and
   (c) water;
   wherein said composition has a pH from about 5.5 to 7.1, and wherein storage of the composition as a ready-to-use and injectable composition for 1 month at 40° C. results in a fludarabine phosphate impurity concentration of no more than about 0.34 percent, and/or wherein storage of the composition as a ready-to-use and injectable composition at 27.5° C. for 7 months results in a fludarabine phosphate impurity concentration of less than 0.94 percent.

2. An aqueous composition according to claim 1, wherein said composition has an enhanced stability, wherein the enhanced stability is such that storage of said aqueous composition at a temperature above 8° C. results in an impurity level less than that formed during storage at a temperature above 8° C. of a second aqueous fludarabine phosphate composition that differs from said fludarabine phosphate composition only in that the second composition has a pH of 7.7.

3. An aqueous composition according to claim 1, wherein said composition has an enhanced stability, wherein the enhanced stability is such that storage of said aqueous composition at a temperature between 20° C. and 40° C. results in an impurity level less than that formed during storage at a temperature between 20° C. and 40° C. of a second aqueous fludarabine phosphate composition that differs from said fludarabine phosphate composition only in that the second composition has a pH of 7.7.

4. An aqueous composition according to claim 2, wherein said composition has a pH from about 6.5 to 7.1.

5. An aqueous composition according to claim 2, wherein said composition has a pH from about 6.7 to 6.9.

6. An aqueous composition according to claim 2, wherein the concentration of fludarabine phosphate is between 10 mg/mL and 40 mg/mL.

7. An aqueous composition according to claim 5, wherein the concentration of fludarabine phosphate is between 20 mg/mL and 30 mg/mL.

8. An aqueous composition according to claim 6, wherein the concentration of fludarabine phosphate is between 24 mg/mL and 26 mg/mL.

9. An aqueous composition according to claim 2, further comprising a buffer.

10. An aqueous composition according to claim 2, further comprising a tonicity agent selected from the group of NaCl and dextrose.

11. An aqueous composition according to claim 2, wherein said base is selected from the group of NaOH, NH$_4$OH and KOH.

12. A ready-to-use injectable aqueous pharmaceutical composition comprising:
    (a) between 0.5 mg/mL and 50 mg/mL fludarabine phosphate;
    (b) a base;
    (c) a buffer; and
    (d) water;
    wherein said composition has a pH from about 5.5 to 7.1, and wherein storage of the composition as a ready-to-use and injectable composition for 1 month at 40° C. results in a fludarabine phosphate impurity concentration of no more than about 0.34 percent, and/or wherein storage of the composition as a ready-to-use and injectable composition at 27.5° C. for 7 months results in a fludarabine phosphate impurity concentration of less than 0.94 percent.

13. An aqueous composition according to claim 12, wherein said composition has an enhanced stability, wherein the enhanced stability is such that storage of said aqueous composition at a temperature above 8° C. results in an impurity level less than that formed during storage at a temperature above 8° C. of a second aqueous fludarabine phosphate composition that differs from said fludarabine phosphate composition only in that the second composition has a pH of 7.7.

14. An aqueous composition according to claim 12, wherein said composition has an enhanced stability, wherein the enhanced stability is such that storage of said aqueous composition at a temperature between 20° C. and 40° C. results in an impurity level less than that formed during storage at a temperature between 20° C. and 40° C. of a second aqueous fludarabine phosphate composition that differs from said fludarabine phosphate composition only in that the second composition has a pH of 7.7.

15. An aqueous composition according to claim 14, wherein said composition has a pH from about 6.5 to 7.1.

16. An aqueous composition according to claim 14, wherein said composition has a pH from about 6.7 to 6.9.

17. An aqueous composition according to claim 14, wherein the concentration of fludarabine phosphate is between 10 mg/mL and 40 mg/mL.

18. An aqueous composition according to claim 17, wherein the concentration of fludarabine phosphate is between 20 mg/mL and 30 mg/mL.

19. An aqueous composition according to claim 17, wherein the concentration of fludarabine phosphate is between 24 mg/mL and 26 mg/mL.

20. An aqueous composition according to claim 13, further comprising a tonicity agent selected from the group of NaCl and dextrose.

21. An aqueous composition according to claim 13, wherein said base is selected from the group of NaOH, NH$_4$OH and KOH.

22. An aqueous composition according to claim 1 wherein said composition has a pH of from about 5.5 to 6.7.

23. An aqueous composition according to claim 12 wherein said composition has a pH of from about 5.5 to 6.7.

24. An aqueous composition according to claim 1 wherein said composition has a pH of from about 5.5 to 6.9.

25. An aqueous composition according to claim 12 wherein said composition has a pH of from about 5.5 to 6.9.

* * * * *

UNITED STATES PATENT AND TRADEMARK OFFICE
CERTIFICATE OF CORRECTION

PATENT NO. : 7,153,840 B2
APPLICATION NO. : 10/445306
DATED : December 26, 2006
INVENTOR(S) : Mirejovsky et al.

It is certified that error appears in the above-identified patent and that said Letters Patent is hereby corrected as shown below:

Column 1
Line 17, change "antineoplastic" to --anti-neoplastic--
Line 52, change "7.7." to --7.7--

Column 3
Line 12, change "composition A, having" to --composition A having--
Line 14, change "composition B, has" to --composition B has--
Line 53, change "Typically the" to --Typically, the--
Line 67, change "invention NaOH" to --invention are NaOH--

Column 4
Line 5, change "Typically the" to --Typically, the--
Line 12, change "iminotris" to --aminotris--
Line 14, change "and (3-N-morpholino]" to --and (3-[N-morpholino]--
Line 32, change "diseases including" to --diseases, including--
Line 35, change "nonlymphatic" to --non-lymphatic--

Column 5
Line 26, change "1 months" to --1 month--
Line 31, change "temperatures also is shown" to --temperatures is also shown--

Column 6
Line 12, change "Mannitol" to --mannitol--
Line 13, change "Water for Injection" to --water for injection--
Line 17, change "Injection" to --injection--
Line 24-25, change "Water for Injection" to --water for injection--
Line 27-28, change "Water for Injection" to --water for injection--
Line 32, change "an fludarabine" to --a fludarabine--

Column 7
Line 53, change "group of" to --group consisting of--
Line 56, change "group of" to --group consisting of--

UNITED STATES PATENT AND TRADEMARK OFFICE
CERTIFICATE OF CORRECTION

PATENT NO. : 7,153,840 B2
APPLICATION NO. : 10/445306
DATED : December 26, 2006
INVENTOR(S) : Mirejovsky et al.

It is certified that error appears in the above-identified patent and that said Letters Patent is hereby corrected as shown below:

<u>Column 8</u>
Line 46-47, change "group of" to --group consisting of--
Line 49, change "group of" to --group consisting of--
Line 51, change "claim 1 wherein" to --claim 1, wherein--
Line 53-54, change "claim 12 wherein" to --claim 12, wherein--
Line 55, change "claim 1 wherein" to --claim 1, wherein--
Line 57-58, change "claim 12 wherein" to --claim 12, wherein--

Signed and Sealed this

Second Day of September, 2008

JON W. DUDAS
*Director of the United States Patent and Trademark Office*